United States Patent [19]

Bader et al.

[11] 4,405,781

[45] Sep. 20, 1983

[54] METHOD FOR PREPARING SALTS OF 6-CHLOROPURINE

[75] Inventors: Henry Bader, Newton Center; Yunn H. Chiang, Andover, both of Mass.

[73] Assignee: Polaroid Corporation, Cambridge, Mass.

[21] Appl. No.: 238,055

[22] Filed: Mar. 2, 1981

[51] Int. Cl.³ ........................................... C07D 473/40
[52] U.S. Cl. ..................................... 544/264; 424/253
[58] Field of Search .......................................... 544/264

[56] References Cited

U.S. PATENT DOCUMENTS

| | | | |
|---|---|---|---|
| 598,502 | 2/1898 | Fisher | 544/264 |
| 2,746,961 | 5/1956 | Hitchings | 260/252 |
| 2,832,781 | 4/1958 | Hitchings et al. | 544/264 |
| 3,314,938 | 4/1967 | Kawashima et al. | 544/264 |
| 3,517,006 | 6/1970 | Fujimoto et al. | 544/264 |

OTHER PUBLICATIONS

Ferguson, Textbook of Organic Chemistry, pp. 266-267 (1965).
Nasutavicus et al., J. Het. Chem., 11, 77-78 (1974).
Bendich et al., J.A.C.S., 76 6073-6077 (1954).
Beaman et al., J. Appl. Chem., 12, 432-437 (1962).
CA, 67, 82224w (1967).

*Primary Examiner*—Nicholas S. Rizzo
*Attorney, Agent, or Firm*—Gaetano D. Maccarone

[57] ABSTRACT

There is described a novel method for preparing and isolating novel salts of 6-chloropurine and strong acids. According to the method hypoxanthine is reacted with phosphorus oxychloride in the presence of an organic base to form 6-chloropurine, a solvent is added to the reaction mixture and the latter is reacted with a strong acid to form a 6-chloropurine salt which is then isolated. In a preferred embodiment 6-chloropurine is freed from the salt with water, preferably in the presence of a base. In another preferred embodiment the 6-chloropurine is aminated with various amines.

12 Claims, No Drawings

METHOD FOR PREPARING SALTS OF 6-CHLOROPURINE

BACKGROUND OF THE INVENTION

The present application relates to a method for preparing and isolating salts of 6-chloropurine with strong acids and to the novel salts prepared by the method.

Various methods for preparing 6-chloropurines are known in the art. W. A. Nasutavicus et al., J. Het. Chem., 11, 77(1974) disclose treating hypoxanthines with phosphorus pentasulfide to give the corresponding mercaptopurines and converting the latter to 6-chloropurines by chlorination with chlorine in hydrochloric acid or acetonitrile.

The chlorination of hypoxanthines with phosphorus oxychloride in the presence of N,N-dimethyl- or diethylaniline is well documented in the literature. Bendich, et al., J. Am. Chem. Soc., 76, 6073(1954) disclose the preparation of 6-chloropurine by the treatment of hypoxanthine with phosphorus oxychloride in the presence of N,N-dimethylaniline via continuous extraction with ether from an acidic aqueous solution, G. H. Hutchins et al have disclosed, in U.S. Pat. No. 2,746,961, that 6-chloropurine can be recovered from the chlorination mixture with methanol after removal of excess phosphorus oxychloride. The isolation of 6-chloropurine from acidic aqueous solution by toluene extraction (Japanese Pat. No. 6,918, 1967) and by salting out with salt (Beaman et al., J. Appl. Chem. 12, 432, 1962) have been reported.

The known methods for preparing 6-chloropurine are not entirely satisfactory because of the difficulties in isolating the product from the reaction mixture. The isolation of the product by continuous solvent extraction is a long and tedious process and is not convenient for large scale preparation of the compound.

The present application is directed to a method for preparing and isolating salts of 6-chloropurine with strong acids which can be converted conveniently to 6-chloropurine.

SUMMARY OF THE INVENTION

It is an object of this invention to provide a method for preparing salts of 6-chloropurine and strong acids.

It is another object to provide a method which includes a convenient technique for isolating the product.

It is a further object to provide a method which gives a product of very high purity.

Still another object is to provide a method which gives high yields of the product.

A further object is to provide novel compounds which are salts of 6-chloropurine and strong acids.

Another object is to provide a method for preparing 6-chloropurine.

Yet another object is to provide a method for preparing various 6-aminopurines such as alkyl-, aralkyl-, or arylaminopurines.

BRIEF SUMMARY OF THE INVENTION

These and other objects and advantages are accomplished in accordance with the invention by providing a novel method for preparing and isolating novel salts of 6-chloropurine and strong acids comprising reacting hypoxanthine with phosphorus oxychloride in the presence of an organic base such as a dialkylaniline to form 6-chloropurine, subsequently adding a solvent to the reaction mixture and then reacting the latter with a strong acid such as hydrochloric acid to form a 6-chloropurine salt which is isolated. In a preferred embodiment 6-chloropurine is freed from the salt with water, optionally and preferably in the presence of a base such as ammonium hydroxide, to obtain 6-chloropurine. According to another preferred embodiment 6-chloropurine is aminated by reaction with various amines such as alkylamines, aralkylamines and arylamines to form 6-aminopurines.

It has been found that by preparing and isolating the 6-chloropurine salts according to the invention high yields of a very high purity product can be obtained. Moreover, the preparation of 6-chloropurine from a 6-chloropurine salt which has previously been isolated from the reaction mixture avoids the time consuming continuous solvent extraction practiced in the prior art processes. Accordingly, the method of the invention is particularly advantageous for large scale commercial preparation of 6-chloropurine.

DESCRIPTION OF THE PREFERRED EMBODIMENTS

The method of the invention proceeds according to the following general reaction sequence.

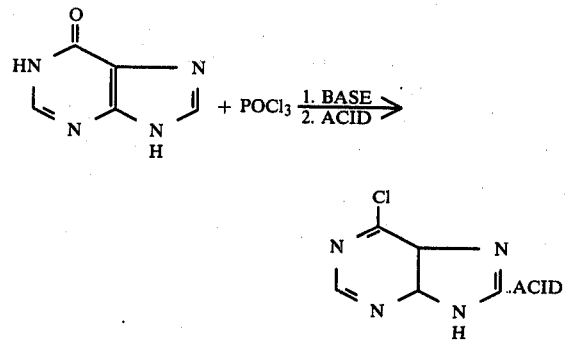

The starting materials for the method are commercially available and can be made by reactions which are known in the art. According to the method of the invention initially the hypoxanthine and phosphorus oxychloride are reacted in the presence of an organic base to form 6-chloropurine. The base, which does not take part in the reaction, should be one which is not reactive with the 6-chloropurine which is formed. Any suitable organic base may be used such as, for example, dialkylanilines such as N,N-dimethyl- or N,N-diethylaniline, quinoline, pyridine, substituted pyridines or the like.

Any excess phosphorus oxychloride is removed from the reaction mixture such as by vacuum distillation with an external oil bath having a temperature below about 70° C. Subsequently a solvent for 6-chloropurine such as methylene chloride or chloroform is added to the reaction mixture and the latter is reacted with a strong acid to form a 6-chloropurine salt. Any suitable strong acid may be used such as, for example, hydrochloric acid, methanesulfonic acid, sulfuric acid, etc. The reaction of 6-chloropurine with the strong acid is preferably carried out at low temperature such as in an ice/water bath.

The 6-chloropurine-acid salt may precipitate from the reaction medium as a solid or a liquid. The hydrochloric acid and methansulfonic acid salts of 6-chloropurine precipitate from methylene chloride as solids; the sulfuric acid salt of 6-chloropurine separates from methylene chloride as an oily material.

The choice of the base, acid and solvent to be employed in any particular instance should be such as to allow for the complete separation of 6-chloropurine as the salt of the acid from the base as the salt of the same acid. For example, the hydrochloric acid salt of 6-chloropurine is insoluble in methylene chloride whereas the hydrochloric acid salt of N,N-dimethylaniline is soluble in that solvent. Thus, in a preferred embodiment of the invention the base is N,N-dimethylaniline, the acid is hydrochloric acid and the solvent is methylene chloride. The 6-chloropurine-HCl salt which is formed readily precipitates out of solution and is easily collected such as by filtration, thus providing an advantageous technique for separating the 6-chloropurine salt from the N,N-dimethylaniline salt.

The formation of the 6-chloropurine salt by reaction with acid was unexpected. Bendich et al., J. Am. Chem. Soc., previously cited, reported that the formation of a variously colored complex between 6-chloropurine and N,N-dimethylaniline made the isolation of 6-chloropurine through solvent extraction impossible. The complex had to be broken by mixing with crushed ice and subsequent adjustment of pH above 11 with aqueous sodium hydroxide solution. It has now been found by applicants that 6-chloropurine, while a very weak base, is capable of forming salts with strong acids.

As discussed previously the novel 6-chloropurine salts of the invention can be converted conveniently to 6-chloropurine by freeing the 6-chloropurine from the salt with water, optionally and preferably in the presence of a base. The reaction is illustrated as follows:

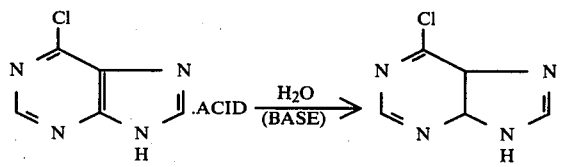

After being collected and washed to remove any contaminants the salt is converted to 6-chloropurine. It is preferred to employ a base to neutralize the solution since higher yields are typically obtained. Any suitable base may be used such as, for example, ammonium hydroxide, sodium hydroxide, potassium hydroxide, sodium bicarbonate, sodium acetate or the like. The pH of the solution should be controlled such that it does not become basic, for example, above about 7.0. Ammonium hydroxide is preferred because of the formation of soluble ammonium chloride; the 6-chloropurine is much less soluble in this environment and salts out readily, thus providing a very convenient separation. It has been found that the highest yields of 6-chloropurine are obtained by adding sufficient ammonium hydroxide to adjust the pH of the aqueous solution to the range of from about 6.5 to about 6.7.

As disclosed previously, according to a preferred embodiment of the invention, 6-chloropurine is aminated by reaction with various amines such as dialkylamines or aralkylamines to form 6-aminopurines such as 6-dodecylaminopurine or 6-benzylaminopurine. The reaction may be illustrated as follows:

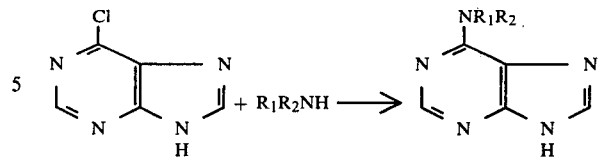

where $R_1$ can be alkyl, aralkyl such as benzyl or aryl such as phenyl and naphthyl and $R_2$ can be H, alkyl or aralkyl. This reaction can be carried out in a solvent such as methyl cellosolve or n-propanol for a period of from about 20 to about 40 minutes.

The invention will now be described further in detail with respect to specific preferred embodiments thereof by way of examples, it being understood that these are intended to be illustrative only and the invention is not limited to the materials, conditions, processes parameters, etc. which are recited therein. All parts and percentages are by weight unless otherwise specified.

EXAMPLE I

A mixture of 50 g (0.368 mole) of hypoxanthine, 120 ml. of N,N-dimethylaniline and 500 ml. of phosphorus oxychloride was refluxed for 20 minutes. Excess phosphorus oxychloride was removed by vacuum distillation with an external oil bath having a temperature below 70° C. and 1.0 liter of methylene chloride was added to the red oily residue. The red methylene chloride solution was cooled in an ice water bath and hydrogen chloride gas was bubbled through the solution until the solution turned a bright yellow color. After stirring the reaction mixture overnight, nitrogen was passed through the solution for 1.5 hours to remove excess hydrogen chloride. The product was collected by filtration, washed with two 150 ml. portions of hot methylene chloride and dried to give 59.3 g (99% yield) of 6-chloropurine hydrochloride, as a cream colored solid, $\lambda$ max $(H_2O)=264$ nm, $\epsilon=9.32\times10^3$.

To 70 ml. of water there was added 36.4 g (0.19 mole) of 6-chloropurine hydrochloride with vigorous stirring. Initially a thick paste was formed; after mixing for a short time the paste thinned out. The solution was stirred for 15 minutes at $-12°$ C. in an ice-methanol bath and the pH was adjusted to 6.7 with concentrated ammonium hydroxide. The product grew in large particles after neutralization. The mixture was placed in a refrigerator for one hour and then the yellow precipitate was collected by filtration. The filter cake was washed with 15 ml. of ice water and dried in a vacuum oven at 55° C. to give 25.9 g. (91% yield) of 6-chloropurine, $\lambda$ max $(H_2O)=264$ nm, $\epsilon=9.10\times10^3$.

EXAMPLE II

A mixture of 6-chloropurine (2.5 g, 0.016 mole) and n-dodecylamine (7.4 g, 0.04 mole) in 40 ml. of n-propanol was refluxed for 5 hours. The reaction mixture was stirred at room temperature for 1 hour and cooled with water (15° C.) for another hour. The product was collected by filtration, washed by two 5 ml. portions of n-propanol and dried in a vacuum oven overnight to give 4.5 g (92% yield) of 6-n-dodecylaminopurine, a colorless solid, m.p. 159°–160° C., $\lambda$ max $(H_2O)=268$ nm, $\epsilon=17.3\times10^3$.

Two grams of the product were stirred with 50 ml. of methylene chloride for 15 minutes. The solution was filtered and the precipitate washed twice with 25 ml. of methylene chloride and dried to give 1.94 g of 6-n-dodecylaminopurine, m.p. 160°–161° C.

EXAMPLE III

A mixture of 5 g (0.0368 mole) of hypoxanthine, 12.5 ml of N,N-dimethylaniline and 150 ml of phosphorus oxychloride was refluxed for 40 minutes. Excess phosphorus oxychloride was removed by vacuum distillation with an external oil bath having a temperature below 70° C. and 200 ml of methylene chloride were added to the oily residue. The red methylene chloride solution was cooled in an ice bath and 6 g (0.063 mole) of methanesulfonic acid were added slowly. The mixture was left in an ice bath with stirring for 1 hour and then filtered to give 7.20 g (78% yield) of 6-chloropurine methanesulfonate as a light yellow solid.

To 15 ml of water there were added 5 g of 6-chloropurine methansulfonate with vigorous stirring. After stirring for 15 minutes at room temperature the mixture was allowed to stand in a freezer for 1 hour after which the light yellow precipitate which formed was collected by filtration. The filter cake was washed with 5 ml of ice water and dried in a vacuum oven at 55° C. to give 2.6 g (84% yield) of 6-chloropurine, $\lambda$ max $(H_2O) = 265$ nm, $\epsilon = 9.22 \times 10^3$.

EXAMPLE IV

A mixture of 5 g (0.0368 mole) of hypoxanthine, 12.5 ml of N,N-dimethylaniline and 150 ml of phosphorus oxychloride was refluxed for 40 minutes. Excess phosphorus oxychloride was removed by vacuum distillation with an external oil bath having a temperature below 70° C. and 200 ml of methylene chloride were added to the oily residue. The red methylene chloride solution was cooled in an ice bath and to it there were added dropwise 6.17 g (0.063 mole) of conc. sulfuric acid. The solution turned yellow and an oily material precipitated. The oily material was separated from the methylene chloride solution in a separatory funnel. Upon standing overnight under a flow of nitrogen the oily material solidified. The solid was treated with water and was converted to 6-chloropurine (contaminated with some dimethylaniline sulfate).

The methylene chloride solution was allowed to stand in a freezer overnight. The resulting precipitate (2 g) was collected by filtration. The solid was treated with water to give 0.7 g of 6-chloropurine, $\lambda$ max $(H_2O) = 265$ nm, $\epsilon = 8.97 \times 10^3$.

Although the invention has been described in detail with respect to various preferred embodiments thereof, these are intended to be illustrative only and not limiting of the invention but rather those skilled in the art will recognize that modifications and variations may be made therein which are within the spirit of the invention and the scope of the appended claims.

What is claimed is:

1. A method for preparing a salt of 6-chloropurine and a strong acid comprising the steps of:
   (a) reacting hypoxanthine and phosphorus oxychloride in the presence of an organic base to form 6-chloropurine;
   (b) adding a solvent for said 6-chloropurine to the reaction mixture obtained in step (a) and reacting said reaction mixture with a strong acid to form a salt of 6-chloropurine and said acid; and
   (c) isolating said salt.

2. The method as defined in claim 1 wherein in step (a) said organic base is dimethylaniline and in step (b) said solvent is methylene chloride and said strong acid is hydrochloric acid.

3. The method as defined in claim 2 and further including the step (d) of freeing 6-chloropurine from said salt by treatment with water.

4. The method as defined in claim 3 wherein step (d) is carried out in the presence of a base.

5. The method as defined in claim 4 wherein said base in step (d) is ammonium hydroxide.

6. The method as defined in claim 1 and further including the step (d) of freeing 6-chloropurine from said salt by treatment with water.

7. The method as defined in claim 6 wherein step (d) is carried out in the presence of a base.

8. The method as defined in claim 7 wherein said base in step (d) is ammonium hydroxide.

9. The method as defined in claim 7 and further including the step of reacting said 6-chloropurine with an amine represented by the formula $R_1R_2NH$ to form a 6-aminopurine represented by the formula

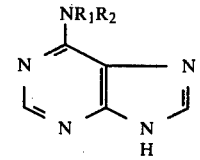

where $R_1$ is alkyl, benzyl, phenyl or naphthyl and $R_2$ is H, alkyl or benzyl.

10. The method as defined in claim 9 wherein $R_1$ is alkyl and $R_2$ is H.

11. The method as defined in claim 10 wherein $R_1$ is alkyl having 12 carbon atoms.

12. The method as defined in claim 9 wherein $R_1$ is benzyl and $R_2$ is H.

* * * * *